(12) United States Patent
Fujii (10) Patent No.: US 9,897,489 B2
(45) Date of Patent: Feb. 20, 2018

(54) PROCESSING APPARATUS AND METHOD OF MEASURING TEMPERATURE OF WORKPIECE IN PROCESSING APPARATUS

(71) Applicant: KOBE STEEL, LTD., Kobe-shi (JP)

(72) Inventor: Hirofumi Fujii, Takasago (JP)

(73) Assignee: Kobe Steel, Ltd., Kobe-shi (JP)

( * ) Notice: Subject to any disclaimer, the term of this patent is extended or adjusted under 35 U.S.C. 154(b) by 244 days.

(21) Appl. No.: 14/769,306

(22) PCT Filed: Mar. 11, 2014

(86) PCT No.: PCT/JP2014/001383
§ 371 (c)(1),
(2) Date: Aug. 20, 2015

(87) PCT Pub. No.: WO2014/162665
PCT Pub. Date: Oct. 9, 2014

(65) Prior Publication Data
US 2015/0377714 A1 Dec. 31, 2015

(30) Foreign Application Priority Data
Apr. 2, 2013 (JP) .................................. 2013-076947

(51) Int. Cl.
*G01K 5/00* (2006.01)
*G01K 9/00* (2006.01)
(Continued)

(52) U.S. Cl.
CPC ................ *G01K 5/50* (2013.01); *C23C 14/52* (2013.01); *C23C 14/541* (2013.01); *C23C 16/52* (2013.01); *G01N 25/00* (2013.01)

(58) Field of Classification Search
None
See application file for complete search history.

(56) References Cited

U.S. PATENT DOCUMENTS 5,350,899 A 9/1994 Ishikawa et al.
6,390,674 B1 * 5/2002 Nakamura ............. G01N 25/16
374/1
(Continued)

FOREIGN PATENT DOCUMENTS

DE 3607368 A1 9/1987
JP 57-197432 A 12/1982
(Continued)

OTHER PUBLICATIONS

International Search Report dated Jun. 17, 2014 for PCT/JP2014/001383 filed on Mar. 11, 2014.
(Continued)

*Primary Examiner* — Erica Lin
(74) *Attorney, Agent, or Firm* — Oblon, McClelland, Maier & Neustadt, L.L.P.

(57) ABSTRACT

A processing apparatus and a method capable of accurately measuring a real temperature of a workpiece contained and heated in a chamber. The processing apparatus includes a chamber containing a workpiece, a measurement piece installed in the chamber, and a measuring unit. The measurement piece is capable of thermal expansion and contraction in response to an internal temperature of the chamber. The measuring unit measures a thermal expansion and contraction amount of the measurement piece to thereby measure the real temperature of the workpiece.

7 Claims, 2 Drawing Sheets

(51) Int. Cl.
*G01K 5/50* (2006.01)
*C23C 14/52* (2006.01)
*C23C 14/54* (2006.01)
*C23C 16/52* (2006.01)
*G01N 25/00* (2006.01)

(56) References Cited

U.S. PATENT DOCUMENTS

| | | | |
|---|---|---|---|
| 2009/0219969 A1 | 11/2009 | Yamamoto | |
| 2011/0005460 A1* | 1/2011 | Hirano | C23C 14/543 |
| | | | 118/712 |
| 2011/0054829 A1* | 3/2011 | Yamada | G01K 17/00 |
| | | | 702/136 |

FOREIGN PATENT DOCUMENTS

| | | |
|---|---|---|
| JP | 63-75795 U | 5/1988 |
| JP | 06-58814 A | 3/1994 |
| JP | 07-27634 A | 1/1995 |
| JP | 7-505744 A | 6/1995 |
| JP | 10-19689 A | 1/1998 |
| JP | 2836876 B2 | 12/1998 |
| JP | 11-202700 A | 7/1999 |
| JP | 3042786 B2 | 5/2000 |
| JP | 2000-206070 A | 7/2000 |
| JP | 2002-350248 A | 12/2002 |
| JP | 2009-212199 A | 9/2009 |
| JP | 2010-151743 A | 7/2010 |
| JP | 4607287 B2 | 1/2011 |
| WO | 90/02216 A1 | 3/1990 |
| WO | WO 92/21011 A1 | 11/1992 |

OTHER PUBLICATIONS

International Preliminary Report on Patentability and Written Opinion dated Oct. 15, 2015 in PCT/JP2014/001383 filed Mar. 11, 2014 (submitting English translation only).

Extended European Search Report dated Oct. 12, 2016 in European Patent Application No. 14778446.6.

* cited by examiner

PROCESSING APPARATUS AND METHOD OF MEASURING TEMPERATURE OF WORKPIECE IN PROCESSING APPARATUS

TECHNICAL FIELD

The present invention relates to a processing apparatus, and a method of measuring a temperature of a workpiece in the processing apparatus

BACKGROUND ART

Heretofore, performed is a surface finishing of a workpiece, such as deposition, nitriding or impregnation, contained in a chamber maintained in a depressurized or vacuum state, by use of PVD or CVD process. In a processing apparatus for performing modification processing such as deposition by use of such PVD or CVD process, it is often performed to finely set a temperature of a workpiece during the processing depending on mechanical properties, adhesion, etc. For example, for enhancing adhesion property between a deposited film and a substrate, they say it is desirable to set the processing temperature to a relatively high value. Meanwhile, from a viewpoint of mechanical properties, there can be a case where setting the temperature of the workpiece to a relatively low value is rather advantageous. That is why the processing temperature of the workpiece, in the PVD or CVD process-based processing, is finely determined depending on mechanical properties, adhesion, etc. This processing temperature requires accurate measurement of a real temperature of the workpiece during the processing.

Other than deposition by PVD or CVD process, the deposition using the processing apparatus as a heating furnace to heat a workpiece, may require a fine temperature management. This case also requires the real temperature of the workpiece to be an accurately measured.

As a technique for the measurement of a real temperature of a workpiece, the following means have been known.

The following Patent Literatures 1 and 2 disclose a measurement method including providing an outer wall of a chamber with a window allowing an inside of the chamber to be visually recognized at a position outside the chamber, and actually measuring a real temperature of a workpiece in the chamber through the window with an infrared radiation thermometer disposed outside the chamber.

The following Patent Literature 3 discloses a method performed in an apparatus for deposition on a surface of a plate-shaped workpiece, the method including bringing a contact-type thermometer into contact with a reverse-side surface of the workpiece on a side opposite to an obverse-side surface thereof on which the deposition is performed, and calculating a real temperature of the workpiece during the processing, from the measured temperature. Such a contact-type thermometer also enables the real temperature of the workpiece to be actually measured.

The following Patent Literature 4 discloses a method including measuring an atmosphere temperature in a heating zone surrounded by a heat insulating material, in order to measure a temperature of the heating zone. The method described in the Patent Literature 4 is not for measuring a temperature of a workpiece during processing but for judging degradation of a thermocouple based on the atmosphere temperature; however, it is suggested that the atmosphere temperature can be utilized as substitute for a real temperature of the workpiece.

The following Patent Literature 5 discloses a method of measuring a temperature of a workpiece composed of a silicon wafer substrate, in a production process with use of vacuum or low-pressure plasma, such as a CVD or sputtering process. This method includes: forming, on a substrate as a workpiece, a thin film made of a polymeric material allowing the thin film to have a variable shape depending on temperature and measuring a temperature of the workpiece during processing, based on the shape variation in the thin film.

The conventional techniques described in the Patent Literatures 1 to 5, however, have the following problems.

The method using a radiation thermometer as described in the Parent Literatures 1 to 2 allows a temperature value measured by the radiation thermometer to be undesirably varied along with a change in emissivity of a surface of a workpiece as a measurement target. This means that a radiation thermometer enables the temperature to be measured only in the case of stable surface. Hence, regarding a workpiece having surface physical property or surface state variable along with a progress of processing as in the above deposition processing, unstable emissivity of the surface of the workpiece may prevent the measurement of the temperature from being performed with a high degree with the radiation thermometer. Moreover, there exists a member other than the workpiece in the chamber, the member also emitting infrared rays, which is likely to cause a large error in a result of the measurement of the real temperature by the radiation thermometer.

Furthermore, in a processing apparatus for deposition, a deposition material adheres also to the observation window, and infrared lays having passed through the window on which the deposition material is adhered are measured by the radiation thermometer. This situation includes a possibility that the deposition material adhering to the window varies intensity (energy amount) of the infrared lays to be measured. This may prevent the real temperature of the workpiece from being accurately measured and may cause a large error in temperature measured by the radiation thermometer.

The measurement method by use of a contact-type thermometer as in the Patent Literature 3 is intended for a workpiece statically placed inside a chamber, in principle. With this measurement method, which uses a contact-type thermometer, it is difficult to measure the temperature of the workpiece during the processing because the contact-type thermometer cannot be kept in contact with the moving workpiece placed on a turntable or the like. Therefore, it is not realistic to employ the measurement technique described in the Patent Literature 3 in a CVD or PVD process which generally involves turn and/or revolution of a workpiece.

Besides, PVD process such as arc ion plating is sometimes performed by providing a potential difference between a chamber and a workpiece. This requires a thermocouple and means for extracting an output signal of the thermocouple with electrical insulation of the output signal from the chamber for insertion of the contact-type thermometer into the chamber from outside to bring it into contact with the workpiece, thus significantly complicating the structure of the processing apparatus.

The method including measuring an atmosphere temperature as in the Patent Literature 4 cannot be employed except the case where the relationship between a temperature (real temperature) of a workpiece and the atmosphere temperature has been accurately figured out during processing. In the case of constant condition of a shape or process or the like of a workpiece, the real temperature of the workpiece can be accurately calculated from the atmosphere temperature; on contrary, in the case of inconstant condition and the like of a shape or process of a workpiece, the real temperature of the workpiece cannot be accurately calculated from the atmosphere temperature.

The method described in the Patent Literature 5, including extracting the thin film outside a chamber and determining a history of temperature change based on the change in the shape of the extracted thin film, is incapable of continuous measurement of the real temperature of the workpiece during processing.

CITATION LIST

Patent Literature

Patent Literature 1: JP 2836876B
Patent Literature 2: JP 06-058814A
Patent Literature 3: JP 3042786B
Patent Literature 4: JP 4607287B
Patent Literature 5: JP 2002-350248A

SUMMARY OF INVENTION

The present invention has been made in view of the above problems, and an object thereof is to provide a processing apparatus and a workpiece temperature measurement method in the processing apparatus, the processing apparatus and method being capable of accurately measuring a real temperature of the workpiece while performing the processing of the workpiece contained in a chamber, even with a variation in a surface physical property or surface state of the workpiece during processing of the workpiece, or even with the movement of the workpiece in the chamber.

Provided by the present invention is a processing apparatus for modification processing of a workpiece, comprising: a chamber containing therein the workpiece; a measurement piece installed in the chamber, the measurement piece being capable of thermal expansion and contraction in response to an internal temperature of the chamber; and a measuring unit configured to measure a thermal expansion or contraction amount of the measurement piece to thereby determine a real temperature of the workpiece.

The term "real temperature" as used herein means an actual temperature of the workpiece itself.

The present invention also provides a method of measuring a temperature of a workpiece in a processing apparatus for modification processing of the workpiece. The method comprises: installing a measurement piece in a chamber containing therein the workpiece, the measurement piece being capable of thermal expansion and contraction in response to an internal temperature of the chamber; and measuring a thermal expansion or contraction amount of the measurement piece to thereby determine a real temperature of the workpiece.

DESCRIPTION OF EMBODIMENTS

Figure 1:
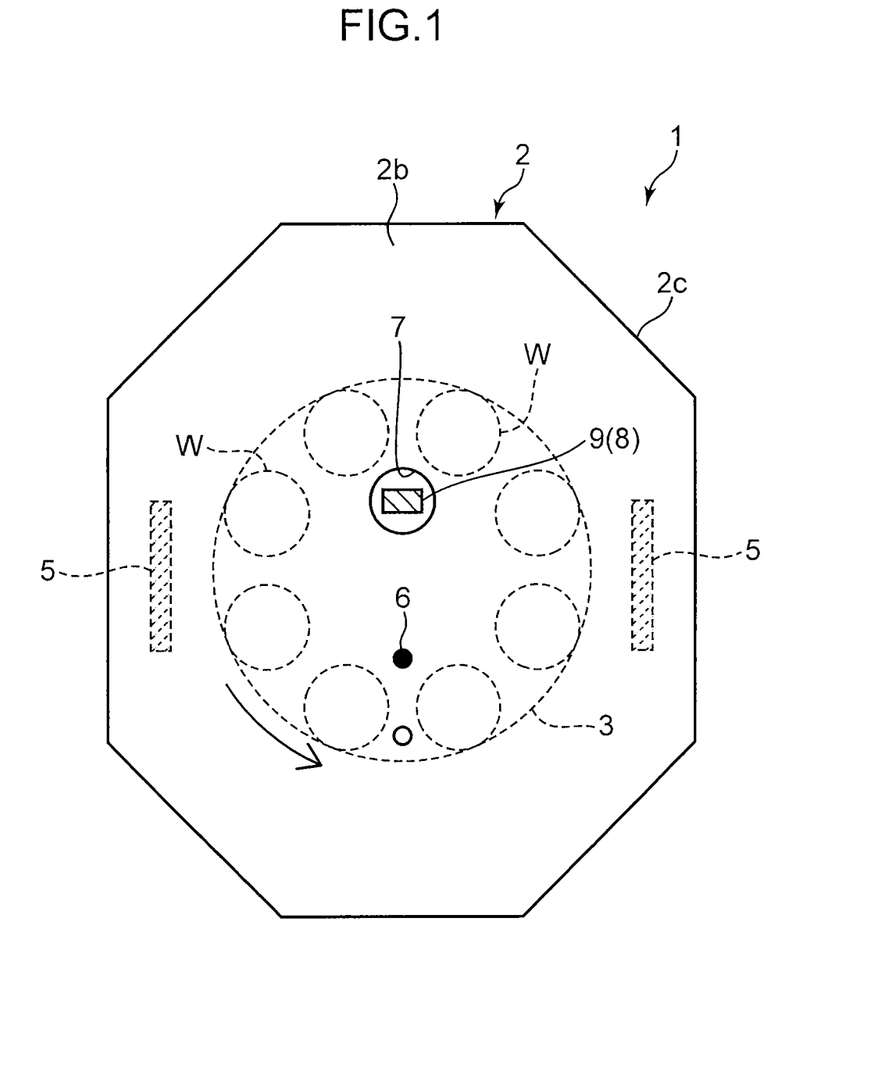
FIG. 1 is a top plan view of a processing apparatus according to one embodiment of the present invention.
Figure 2:
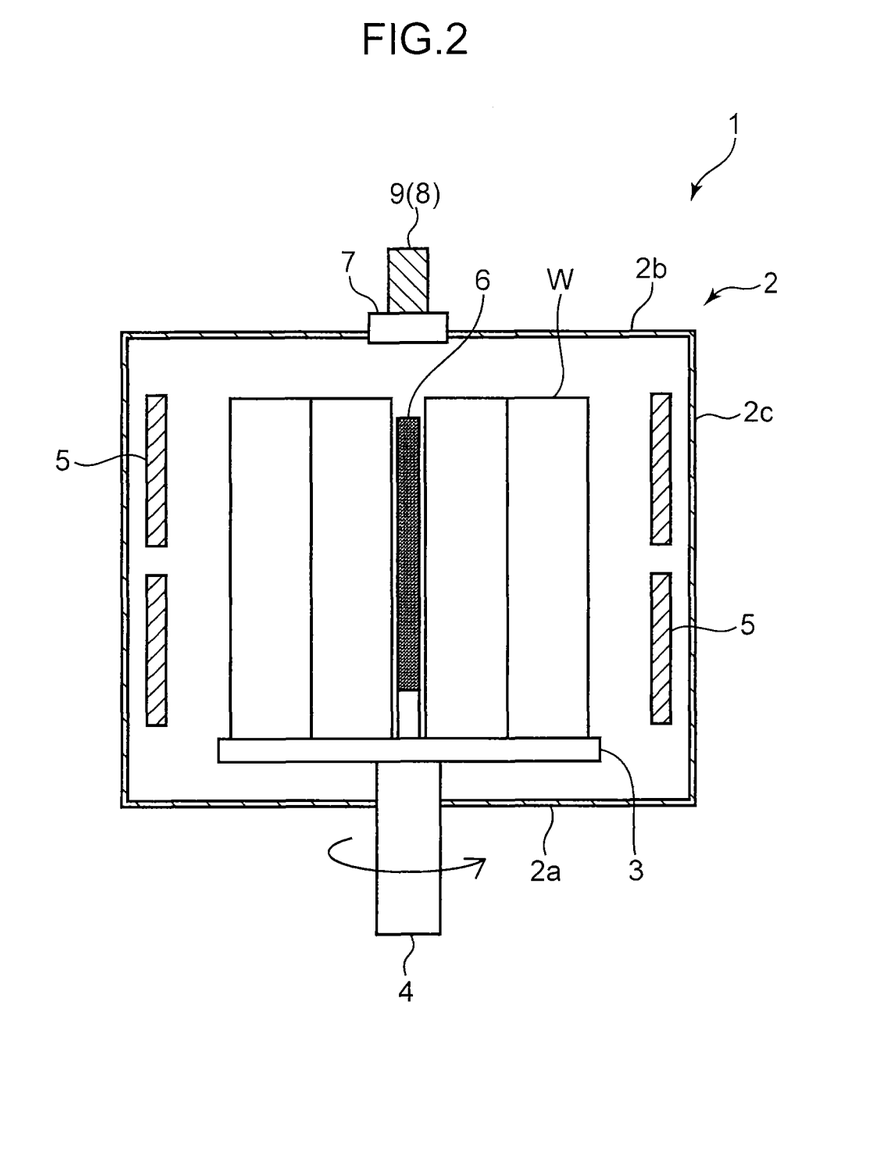
FIG. 2 is a front view of the processing apparatus

FIG. 1 and FIG. 2 show a processing apparatus 1 according to one embodiment of the present invention. The processing apparatus 1 comprises at least a chamber 2 capable of containing therein a plurality of workpieces. Examples of processing apparatuses similar to this processing apparatus 1 include a processing apparatus for subjecting a surface of a workpiece W to surface finishing, such as deposition, nitriding or impregnation by use of PVD or CVD process, and a processing apparatus for heating a workpiece W in a vacuum or under reduced pressure to modify a surface of the workpiece W, and the present invention encompasses these processing apparatuses. This embodiment will be described by taking as an example the processing apparatus 1 which is a PVD processing apparatus for deposition on a surface of a workpiece W by use of arc ion plating.

As shown in FIGS. 1 and 2, the chamber 2 is a box-shaped member capable of containing therein the workpieces W. The chamber 2 is formed so as to have an interior capable of being gas-tightly sealed against the outside thereof. In other words, the chamber 2 is capable of maintaining an internal space of the chamber 2, i.e., a space in which the workpieces W are contained, in a vacuum or depressurized state.

The chamber 2 in this embodiment is formed in a box shape including a bottom wall 2a, a top wall 2b and a cross-sectionally octagonal-shaped sidewall 2c.

The processing apparatus 1 according to this embodiment further comprises a turntable 3. The turntable 3 is provided inside the chamber 2 and located in an approximately central region of the bottom wall 2a. The turntable 3 is configured to allow the workpieces W, i.e., target objects to be processed, to be placed thereon. The workpieces W thus placed on the turntable 3 has a surface on which a hard film (coating), such as a TiN, ZrN or CrN film (coating), is formed through physical vapor deposition process (PVD process).

Each of the workpieces W shown in FIGS. 1 and 2 has a cylindrical-shaped outer peripheral surface. However, the shape of a workpiece as a target object of the processing apparatus according to the present invention is not particularly limited. For example, the present invention can be also applied to a so-called work set including a plurality of small members and having a generally cylindrical shape based on the combination of the small members and also a workpiece having a shape other than a cylindrical shape (e.g., prismatic shape).

The turntable 3 is formed into a shape having an upper surface allowing the workpieces W to be placed thereon, specifically, a shape of flat and circular disc. The turntable 3 is installed turnably about a vertical turning axis set at a center of a bottom surface of the chamber 2, being capable of rotating each of the workpieces W placed on the upper surface around the turning axis together with the turning of the turntable 3, that is, being capable of revolving the workpiece W. Specifically, the turntable 3 (revolving table) is connected to a rotary shaft 4 located under the turntable 3. The rotary shaft 4 has a rod shape whose axis is coincident with the aforementioned turning axis. The rotary shaft 4 vertically penetrates through the bottom wall 2a of the chamber 2. The rotary shaft 4 has an upper end and a lower end. The upper end of the rotary shaft 4 is fixed to a lower surface of the turntable 3, while the lower end of the rotary shaft 4 is connected to a not-graphically-shown rotational drive device including a motor. Between the bottom wall of the chamber 2 and the rotary shaft 4A is provided a not-graphically-shown sealing mechanism permitting the rotary shaft 4 to be rotated relatively to the bottom wall 2a while ensuring gas-tightness of the chamber 2. The rotational drive device including the motor turns the rotary shaft 4 and the turntable 3 connected to the rotary shaft 4, about the turning axis.

The plurality of workpieces W are placed on an outer peripheral region of the upper surface of the turntable 3, spaced circumferentially of the turntable 3. In the present embodiment, eight of the workpieces W are disposed. Accompanying the turn of the turntable 3 about the turning axis, the workpieces W are moved in the chamber 2 along a circular orbit (revolution path) around the turning axis.

Each of evaporation sources 5 is a member formed of a deposition material serving as a raw material for a film to be formed on the surface of the workpiece W. The graphically shown evaporation source 5 is formed of a deposition material and in a plate shape. For example, in the PVD apparatus using arc ion plating, used is metal such as Ti, Zr or Cr, as the evaporation source 5.

Each of the evaporation sources 5 is installed along an inner surface of the sidewall 2c of the chamber 2, in such a posture that the thickness direction thereof is coincident with the thickness direction of the sidewall 2c of the chamber 2. The evaporation sources 5 are, thus, located radially outward of the turntable 3. The evaporation sources 5, each formed in a plate shape as above, are disposed at respective positions (four positions in the shown embodiment) so as to direct respective normal lines passing through respective center positions of the evaporation sources 5 toward a center of the turntable 3. The deposition material making up the evaporation sources 5 is vaporized, by utilization of plasma or the like, into particles, and adhered to the surfaces to the workpieces W to contribute to deposition.

The processing apparatus 1 according to this embodiment further comprises a measurement piece 6 and a measuring unit 8. The measurement piece 6 is installed inside the chamber 2, being capable of thermal expansion and contraction in response to an internal temperature of the chamber 2. The measuring unit 8 is installed outside the chamber 2 and configured to measure a thermal expansion and contraction amount of the measurement piece 6. Specifically, the chamber 2 is provided with an observation window 7 enabling the measurement piece 6 installed inside the chamber 2 to be observed at a position outside the chamber 2. The measuring unit 8 includes a laser displacement meter 9 and measures the thermal expansion and contraction amount of the measurement piece 6 through the observation window 7, thereby determining the temperature of the workpieces W.

Next will be described details of the measurement piece 6, the observation window 7 and the measuring unit 8.

The measurement piece 6 is thermally expanded or thermally contracted at a given rate with variation in temperature. This enables the temperature to be determined by measurement of the thermal expansion and contraction amount (thermally elongated and contracted length) of the measurement piece 6. Preferably, the measurement piece 6 is shaped into a long rod extending in a specific longitudinal direction and made of the same material as a material making up the workpieces W, or of a material having a linear expansion coefficient close to that of the material making up the workpieces W, so as to be thermally expanded and contracted as same as the workpieces W. The measurement piece 6 thus made of the same material as the material of the workpieces W or of a material having a linear expansion coefficient close to that of the material of the workpieces W can be subjected to deposition under the same conditions as those for the workpieces W in a deposition apparatus, which enables the temperature of the workpieces W to be accurately evaluated by use of the measurement piece 6.

In conformity to the vertically long shape of the workpieces W, the measurement piece 6 is also formed in a long rod shape having approximately the same vertical length as that of the workpieces W. In order to restrain the measurement piece 6 from imparting adverse influence on a state of deposition for each of the workpieces W, the measurement piece 6 is given a shape having a circular cross-section with a diameter smaller than that of the workpiece W. As the measurement piece 6 shown in FIGS. 1 and 2, used is a round rod-shaped measurement piece in accordance with the cylindrical-shaped workpieces W.

The measurement piece 6 is installed so as to vertically stand up on the upper surface of the turntable 3. The measurement piece 6 is placed on the turntable 3 together with the workpieces W and located adjacent to and inward of specific one or more of the workpieces W so as to have a temperature equal to the temperature of the workpieces W.

Specifically, a lower end of the measurement piece 6, i.e., a first one of longitudinally opposite ends thereof, is fixed to the upper surface of the turntable 3, while an upper end of the measurement piece 6, i.e., the other, second, end thereof, is upwardly directed. Accordingly, the thermal expansion or contraction of the measurement piece 6 due to the variation in temperature of the measurement piece 6 involves the vertical displacement of the upper end of the measurement piece 6 while the lower end of the measurement piece 6 is fixed to the turntable 3. The thus varying position (height position) of the upper end of the measurement piece 6 in accordance with the vertical expansion and contraction of the measurement piece 6 can be measured by use of the laser displacement meter 9 (laser distance meter), thereby allowing the thermal expansion and contraction amount of the measurement piece 6 to be measured.

As mentioned above, the measurement piece 6 is located on the turntable 3 at a position adjacent to and radially inward of specific one or more of the workpieces W (radially inward of the turntable 3). The reason for disposing the measurement piece 6 at such a position is to prevent the installation of the measurement piece 6 from exerting an influence on deposition for the specific workpieces W. For example, in the case of arc ion plating, arc discharges are generated in the vicinity of respective surfaces of the evaporation sources 5, thereby vaporizing the evaporation sources 5 to emit deposition material therefrom toward the workpieces W. If the measurement piece 6 was disposed on the turntable 3 at a position adjacent to the specific workpieces W and radially outward of the specific workpieces W with respect to centers of the specific workpieces W (e.g., at a position of the white circle on the turntable 3, shown in FIG. 1), the measurement piece 6 hinders the deposition material from reaching the specific workpieces W, thereby generating the possibility of preventing the deposition material from being uniformly formed on the specific workpieces W adjacent to the measurement piece 6. For the reason, the measurement piece 6 is disposed on a side opposite to the evaporation sources 5 across the specific workpieces W, along the radial direction with a center at the turning axis of the turntable 3 (position radially inward of the centers of the specific workpieces W and closer to the turning axis than the centers of the specific workpieces W; position indicated by the black circle in FIG. 1), so as to locate the measurement piece 6 farther away from the associated ones of the evaporation sources 5 than the specific workpieces W. Thus disposing the measurement piece 6 at a position closer to the turning axis than the specific workpieces W reduces the influence of the measurement piece 6 on deposition for the specific workpieces W, enabling uniform deposition to be performed on the specific workpieces W, irrespective of the presence of the measurement piece 6.

The measurement piece 6, fixed to the given position on the turntable 3, can be returned to the same position on an orbital path thereof circumferentially of the turntable 3, every full turn of the turntable 3 about the turning axis. Hence, fixing the measurement point of the laser displacement meter 9 at a single point on an orbit (orbital path) of the measurement piece 6 enables the thermal expansion and contraction amount of the measurement piece 6 to be measured every time the measurement piece 6 reaches the same circumferential position along with turning of the turntable. This enables the temperature of the measurement piece 6, i.e., a real temperature of the workpieces W, to be measured at specific time intervals.

The observation window 7 is formed in a wall making up the chamber 2 and facing the turntable 3, so as to allow the thermal displacement of the upper end of the measurement piece 6 inside the chamber 2 to be measured at a position outside the chamber 2. Specifically, the observation window 7 in this embodiment is provided in a top wall 2b of the chamber 2 and formed of a light-permeable material such as glass so as to allow the laser beam emitted from the laser displacement meter 9 of the measuring unit 8 to pass through the observation window 7. The position of the observation window 7 is set to such a position that the measurement piece 6 passes through a region under the observation window 7, i.e., at a position over the orbital path of the measurement piece 6 on the turntable 3. Disposing the observation window 7 at such a position enables the laser displacement meter 9 of the measuring unit 8 to emit a laser beam to the upper end of the measurement piece 6 from a position just above the upper end, thereby allowing the length of the measurement piece 6 to be reliably and accurately measured.

The measuring unit 8 measures the thermal expansion and contraction amount of the measurement piece 6 to thereby determine the temperature of the workpieces W. The measuring unit 8 includes the laser displacement meter 9 (laser distance meter) configured to measure a relative displacement of the second end (in this embodiment, a vertical displacement of the upper end) to the first end (in this embodiment, the lower end) of the measurement piece 6, and a calculation section configured to calculate the temperature of the workpieces W based on the thermal expansion and contraction amount of the measurement pieces 6 measured by the laser displacement meter 9.

As shown in FIG. 2, the laser displacement meter 9 is configured to determine a displacement of the upper end of the measurement piece 6 which is a target object to be measured through measuring a reflected beam of the emitted laser beam and applying a principle of a triangulation method. The laser displacement meter 9 is disposed just above the observation window 7 in the top wall 2b of the chamber 2, and configured to emit a laser beam toward the measurement piece 6 downward thereof through the observation window 7. Regarding the thus measured displacement (the thermal expansion and contraction amount of the measurement piece 6), a signal is sent to the calculation section.

The laser displacement meter 9 is able to measure the thermal expansion and contraction amount of the measurement piece 6 in a non-contact manner and to perform the measurement at a sampling period enough to follow the maximum speed (e.g., about 5 rpm) of the turntable of the processing apparatus. Further, as regards a temperature measurement in a processing temperature range of about several hundred degrees C. typically required for processing apparatuses, the laser displacement meter 9 is capable of measurement with a sufficient measurement resolution capability, i.e., has good measurement accuracy. This allows the above-mentioned laser displacement meter 9 to be suitably used in the measuring unit 8.

The calculation section is configured to calculate the temperature of the measurement piece 6 by use of the temperature of the measurement piece 6 before measurement or before heating, the linear expansion coefficient of the material used for the measurement piece 6, and the displacement of the upper end of the measurement piece 6 measured by the laser displacement meter 9. Since the temperature of the measurement piece 6 before measurement or before heating and the linear expansion coefficient of the material used for the measurement piece 6 have been already known, the temperature of the measurement piece 6, i.e., the real temperature of the workpieces W, can be unambiguously determined by measuring the displacement using the laser displacement meter 9.

A linear expansion coefficient of a material is not constant with respect to temperature, and a value of the linear expansion coefficient varies depending on in what range the real temperature of the workpiece W lies. Therefore, for further accurately measuring the real temperature of the workpiece W, it is desirable to provide a plurality of linear expansion coefficients to be used in the calculation for each of a plurality of temperature ranges, such as a temperature range of 200 to 300° C., a temperature range of 300 to 400° C. and a temperature range of 400 to 500° C.

While the above processing apparatus 1 is an apparatus for deposition onto the workpieces W by use of PVD or CVD process, the processing apparatus according to the present invention may be also used for aftermentioned ion bombardment processing or heating processing. For example, ion bombardment processing, which is a process of emitting heavy inert gas ions, such as argon ions, generated in a chamber by a plasma discharge before PVD or CVD deposition, emit, to a surface of a workpiece to thereby clean a surface of the resulting substrate, also requires a minute control of a processing temperature of a workpiece W; therefore, it is desirable to employ the aforementioned processing apparatus and a workpiece temperature measurement method, according to the present invention.

Next will be described, a method of measuring the real temperature of the workpieces W by use of the above processing apparatus 1, i.e., one example of a workpiece temperature measurement method of the present invention.

The workpiece temperature measurement method includes: installing the measurement piece 6 capable of thermal expansion and contraction in response to an internal temperature in the chamber 2 containing therein the workpieces W, and measuring the thermal expansion and contraction amount of the measurement piece 6 to thereby determine the real temperature of the workpieces W.

More specifically, the real temperature of the workpieces W is measured in the following manner.

First of all, the plurality of workpieces W are placed on the upper surface of the turntable 3 at respective given positions, and the rotational drive unit including a motor turns the turntable 3 about the turning axis. Thus, each of the workpieces W placed on the turntable 3 is revolved around the turning axis, in the chamber 2.

During the revolution of the workpieces W, the evaporation sources 5 are electrically connected to a minus pole of a non-shown arc power source. On the other hand, an additional electrode is preliminarily provided inside the chamber 2, and electrically connected to a plus pole of the arc power source. The connections give a potential difference between each of the evaporation sources 5 serving as a cathode and the additional electrode serving as an anode to thereby generate discharges on respective surfaces of the evaporation sources 5. The arc discharges vaporize the deposition material from the evaporation sources 5 to emit particles of the deposition material toward the workpieces W. The deposition material is thereby deposited on the workpieces W to establish deposition.

During the deposition, the measurement piece 6 installed at a given position on the turntable 3 is returned to the same circumferential position, every full turn of the turntable 3 about the turning axis. At the moment when the upper end of the measurement piece 6 returned to the same circumferential position passes through the measuring unit 8, the position of the upper end is measured and further the thermal expansion and contraction amount of the measurement piece 6 is measured.

The thermal expansion and contraction amount of the measurement piece 6 thus measured by the measuring unit 8 is processed in the following manner and the real temperature of the workpieces W is thereby calculated.

For example, if the material used for the measurement piece 6 is SUS 304, the measurement piece 6 has a linear expansion coefficient of $18 \times 10^{-6}$ (/° C.). For example, if the measurement piece 6 has a length of 300 mm at a temperature before measurement or before heating of 20° C. and the elongation of the measurement piece 6 measured by the laser displacement meter 9 after measurement or before heating is 2 mm, the temperature T (° C.) of the measurement piece 6 can be calculated based on the following formula (1), being 390° C. The elongation of 2 mm, therefore, indicates that the real temperature T of the workpieces W is 390° C.

$$2 = 300 \times (18 \times 10^{-6}) \times (T - 20) \quad (1)$$

The aforementioned processing apparatus 1 and workpiece temperature measurement method, including measuring the real temperature of the workpieces W based on the thermal expansion and contraction amount of the measurement piece 6, can prevent the surface physical property or the surface state of the workpieces W from exerting influence on accuracy of the temperature measurement, differently from the case of using a radiation thermometer. This makes it possible to perform the processing while accurately measuring the real temperature of the workpieces W even when the deposition likely to vary the surface physical property or surface state of the workpieces W is performed in the deposition apparatus 1.

In the case of measuring infrared rays by use of a radiation thermometer through a window provided in the chamber 2, there is a possibility of difficulty in maintaining accuracy of the temperature measurement because of an influence of the deposition material adhering to the window, infrared rays emitted from a material other than the workpieces W, and the like. In contrast, according to the method of measuring the real temperature of the workpieces W based on the thermal expansion and contraction amount of the measurement piece 6 by use of the laser displacement meter 9, the temperature measurement is less sensitive to dirtiness of the window, thus allows high accuracy of the temperature measurement to be maintained.

The deposition by use of CVD or PVD process often involves moving each of the workpieces W inside the chamber 2 by use of the turntable 3 or the like inside the chamber 2. It is difficult to measure the temperature of a workpiece being moved inside the chamber 2 as described above, by use of an contact-type thermometer configured to measure a temperature of the workpiece W through contact with the workpiece W as a prior art. In contrast, the method of measuring the real temperature of the workpieces W based on the thermal expansion and contraction amount of the measurement piece 6 allows the processing to be performed while accurately measuring the real temperature of the workpieces W, regardless of the movement of the workpieces W.

It should be noted that the present invention is not limited to the above embodiment, but various changes and modifications may be made therein in terms of shape, structure, material, combination, etc., of each component, without departing from the spirit and scope of the invention hereinafter defined. Further, as regards matters which are not explicitly disclosed in the above embodiment, such as operating and processing conditions, various parameters, and size, weight and volume of each component, any value easily assumable to a person having ordinary skill in the art may be employed without departing from a range usually implemented by a persons skilled in the art.

For example, while the processing apparatus according to the above embodiment is a deposition apparatus, the processing apparatus of the present invention also encompasses a heating apparatus for simply performing heating with no deposition, such as a heating furnace (heating furnace incapable of deposition based on PVD process or CVD process or the like). Accordingly, the modification processing to be performed for a workpiece W by the processing apparatus of the present invention also encompasses a heat processing to be performed by the above heating furnace, i.e., a heat processing involving no deposition.

The present invention can be also applied to a deposition apparatus having no heating device such as a heater. Even in this type of deposition apparatus, particles of the deposition material vaporized during deposition can adhere to a workpiece W and become solidified thereon to thereby raise a temperature of the workpiece W. For measurement of such a temperature rise, the technique of the present invention can be employed.

Instead of the measurement of the thermal expansion and contraction amount of the measurement piece 6 through the observation window 7 as in the above embodiment, may be performed a measurement of the thermal expansion and contraction amount of the measurement piece 6 within the chamber 2 by installing the laser displacement meter 9 inside the chamber 2. For this measurement, it is preferable to dispose the laser displacement meter 9 itself in a given protective casing and to install an anti-adhesion plate, a heat shielding plate and/or the like around the laser displacement meter 9 so as to prevent adhesion of the deposition material to an emitting surface of the laser displacement meter 9 and/or heat from exerting influence.

Furthermore, even in the case of impossibility of installing the laser displacement meter 9 except at such a position inside the chamber 2 that the laser displacement meter 9 cannot emit a laser beam directly to the measurement piece 6, the measurement can be performed by use of a mirror adapted to bend a path of the laser beam to be emitted to the measurement piece 6, midway of the path.

As above, according to the invention, provided is a processing apparatus and a workpiece temperature measurement method in the processing apparatus, the processing apparatus and method being capable of accurately measuring a real temperature of the workpiece while performing the processing of the workpiece contained in a chamber, even with a variation in a surface physical property or surface state of the workpiece during processing of the workpiece, or even with the movement of the workpiece in the chamber.

Provided by the present invention is a processing apparatus for modification process of a workpiece, comprising: a chamber containing therein the workpiece; a measurement piece installed in the chamber, the measurement piece being capable of thermal expansion and contraction in response to an internal temperature of the chamber; and a measuring unit configured to measure a thermal expansion or contraction amount of the measurement piece to thereby determine a real temperature of the workpiece.

The measurement piece is preferably formed of a same material as that of the workpiece. This allows the temperature of the workpiece to be more accurately evaluated by use of the measurement piece Preferably, the chamber is provided with an observation window allowing the measurement piece inside the chamber to be observed at a position outside the chamber, the measuring unit being configured to measure the thermal expansion and contraction amount of the measurement piece through the observation window. This makes it possible to measure the thermal expansion and contraction amount of the measurement piece inside the chamber while installing the measuring unit outside the chamber to prevent the measuring unit from receiving influence of an internal state of the chamber.

Preferably, the measurement piece is formed in a rod shape extending along a specific longitudinal direction thereof and the measuring unit is configured to measure the real temperature of the workpiece based on the thermal expansion and contraction amount of the measurement piece along the longitudinal direction. This facilitates the measurement of the thermal expansion and contraction amount of the measurement piece.

More preferably, the measurement piece has longitudinally opposite ends being a first end and a second end, and the measuring unit includes a laser displacement meter configured to emit a measurement laser beam to the second end of the measurement piece to measure a relative displacement of the second end to the first end of the measurement piece.

Preferably, the processing apparatus according to the second preferred embodiment of the present invention further comprises a turntable configured to revolute the workpiece about a turning axis, inside the chamber, wherein: the measurement piece has longitudinally opposite ends being a first end and a second end; the measurement piece is disposed so as to have a longitudinal direction parallel to the turning axis while the first end thereof is fixed to the turntable; and the observation window is provided in a wall of the chamber at a position facing the turntable so as to allow the measuring unit to measure the thermal expansion and contraction amount of the measurement piece at the second end of the measurement piece inside the chamber, at a position outside the chamber. This arrangement facilitates the measurement of the thermal expansion and contraction amount of the measurement piece by the measuring unit.

Preferably, the above processing apparatus further comprises a evaporation source provided inside the chamber to perform deposition on the workpiece, the measurement piece being provided at a position adjacent to the workpiece and on a side opposite to the evaporation source across the workpiece along a radial direction with a center at the turning axis of the turntable. This arrangement makes it possible to restrain the measurement piece from exerting influence on deposition on the workpiece by the evaporation source.

Preferably, the measurement piece is maintained at a same potential as that of the workpiece. This makes it possible to perform a temperature measurement including a measurement of a bias effect (i.e., an effect generated by attracting ions to the workpiece, such as activation, modification, temperature rise, etching, etc., of the surface, resulting from emitting ions to the workpiece), for example, in a process of applying a bias voltage to a workpiece to presses a surface of the workpiece.

The present invention also provides a method of measuring a temperature of a workpiece in a processing apparatus for performing modification process of the workpiece. The method comprises: installing a measurement piece inside a chamber containing therein the workpiece, the measurement piece being capable of thermal expansion and contraction in response to an internal temperature of the chamber; and measuring a thermal expansion and contraction amount of the measurement piece to thereby determine a real temperature of the workpiece.

The invention claimed is:

1. A processing apparatus for modification process of a workpiece, comprising:
   a chamber containing therein the workpiece;
   a measurement piece installed inside the chamber, the measurement piece being capable of thermal expansion and contraction in response to an internal temperature of the chamber;
   a measuring unit configured to measure a thermal expansion and contraction amount of the measurement piece to thereby measure a real temperature of the workpiece; and
   a turntable configured to revolute the workpiece about a turning axis, inside the chamber, wherein:
   the chamber is provided with an observation window allowing the measurement piece inside the chamber to be observed at a position outside the chamber, and the measuring unit is configured to measure the thermal expansion and contraction amount of the measurement piece through the observation window;
   the measurement piece has longitudinally opposite ends being a first end and a second end;
   the measurement piece is disposed so as to have a longitudinal direction parallel to the turning axis while the first end thereof is fixed to the turntable; and
   the observation window is provided in a wall of the chamber at a position facing the turntable so as to allow the measuring unit to measure the thermal expansion and contraction amount of the measurement piece at the second end of the measurement piece inside the chamber, at a position outside the chamber.

2. The processing apparatus as recited in claim 1, wherein the measurement piece is formed of a same material as that of the workpiece.

3. The processing apparatus as recited in claim 1, wherein the measurement piece is formed in a rod shape extending along a longitudinal direction thereof, and the measuring unit is configured to measure the real temperature of the workpiece based on the thermal expansion and contraction amount of the measurement piece along the longitudinal direction.

4. The processing apparatus as recited in claim 3, wherein the measurement piece has longitudinally opposite ends being a first end and a second end, and the measuring unit includes a laser displacement meter configured to emit a measurement laser beam to the second end of the measurement piece to measure a relative displacement of the second end to the first end of the measurement piece.

5. The processing apparatus as recited in claim 1, further comprising a evaporation source provided inside the chamber to perform deposition on the workpiece, wherein the measurement piece is provided at a position adjacent to the workpiece and on a side opposite to the evaporation source across the workpiece along a radial direction with a center at the turning axis of the turntable.

6. The processing apparatus as recited in claim 1, wherein the measurement piece is maintained at a same electrical potential as that of the workpiece.

7. A method of measuring a temperature of a workpiece in a processing apparatus for performing modification process of the workpiece, the method comprising:

installing, inside a chamber containing therein the workpiece, a turntable configured to revolute the workpiece about a turning axis, a measurement piece capable of thermal expansion and contraction in response to an internal temperature of the chamber, the measurement piece having longitudinally opposite ends being a first end and a second end, and being disposed so as to have a longitudinal direction parallel to the turning axis while the first end thereof is fixed to the turntable;

providing, inside the chamber, an observation window allowing the measurement piece inside the chamber to be observed at a position outside the chamber;

measuring a thermal expansion and contraction amount of the measurement piece at the second end of the measurement piece through the observation window to thereby determine a real temperature of the workpiece.

\* \* \* \* \*